United States Patent
Ries et al.

(10) Patent No.: US 11,647,891 B2
(45) Date of Patent: May 16, 2023

(54) ENDOSCOPE DEVICE

(71) Applicant: JOIMAX GMBH, Karlsruhe (DE)

(72) Inventors: Wolfgang Ries, Linkenheim (DE); Martin Germann, Pfinztal (DE)

(73) Assignee: JOIMAX GMBH, Karlsruhe (DE)

(*) Notice: Subject to any disclaimer, the term of this patent is extended or adjusted under 35 U.S.C. 154(b) by 483 days.

(21) Appl. No.: 16/636,540

(22) PCT Filed: Aug. 20, 2018

(86) PCT No.: PCT/EP2018/000405
§ 371 (c)(1),
(2) Date: Feb. 4, 2020

(87) PCT Pub. No.: WO2019/042578
PCT Pub. Date: Mar. 7, 2019

(65) Prior Publication Data
US 2021/0177245 A1 Jun. 17, 2021

(30) Foreign Application Priority Data

Aug. 29, 2017 (DE) .................... 10 2017 008 148.4
Sep. 15, 2017 (DE) .................... 20 2017 004 822.1

(51) Int. Cl.
*A61B 1/00* (2006.01)
*A61B 1/01* (2006.01)
(Continued)

(52) U.S. Cl.
CPC ...... *A61B 1/00087* (2013.01); *A61B 1/00064* (2013.01); *A61B 1/00097* (2022.02); *A61B 1/00121* (2013.01); *A61B 1/00124* (2013.01); *A61B 1/00128* (2013.01); *A61B 1/00135* (2013.01); *A61B 1/00158* (2013.01); *A61B 1/01* (2013.01); *A61B 1/012* (2013.01); *A61B 1/3135* (2013.01); *A61B 5/062* (2013.01); *A61B 34/20* (2016.02); *A61B 2034/2051* (2016.02)

(58) Field of Classification Search
CPC ...................................................... A61B 90/00
See application file for complete search history.

(56) References Cited

U.S. PATENT DOCUMENTS 4,911,148 A * 3/1990 Sosnowski ......... A61B 1/00165
600/164
5,997,473 A 12/1999 Taniguchi et al.
(Continued)

FOREIGN PATENT DOCUMENTS

DE   10 2006 052 886 A1   5/2007
EP   0 894 473 A2          2/1999
(Continued)

*Primary Examiner* — Jermele M Hollington
*Assistant Examiner* — Suresh K Rajaputra
(74) *Attorney, Agent, or Firm* — McGlew and Tuttle, P.C.

(57) ABSTRACT

For determining a precise orientation and positioning of an endoscope in an electromagnetic field, an endoscope device has a proximal insertion head and has a shaft extending distally therefrom having a center axis. The shaft extends with at least one elongated lumen through the device. A sensor rod has at least two sensor coils arranged with finite spacing in relation to one another in the longitudinal direction. The at least two sensor coils are oriented in relation to one another at a finite angle.

13 Claims, 1 Drawing Sheet

(51) Int. Cl.
*A61B 1/012* (2006.01)
*A61B 34/20* (2016.01)
*A61B 1/313* (2006.01)
*A61B 5/06* (2006.01)

(56) References Cited

U.S. PATENT DOCUMENTS

| | | |
|---|---|---|
| 2004/0097805 A1 | 5/2004 | Verard et al. |
| 2007/0164900 A1 | 7/2007 | Schneider et al. |
| 2007/0225559 A1 | 9/2007 | Clerc et al. |
| 2014/0039258 A1* | 2/2014 | Sekiguchi ............... A61B 5/062 |
| | | 600/117 |
| 2014/0317910 A1* | 10/2014 | Govari ................... A61B 5/062 |
| | | 29/602.1 |
| 2021/0153724 A1* | 5/2021 | Ries ................... A61B 17/3472 |

FOREIGN PATENT DOCUMENTS

| | | |
|---|---|---|
| EP | 2 213 220 A1 | 8/2010 |
| EP | 2 269 532 A1 | 1/2011 |
| JP | 2000175862 A | 6/2000 |
| JP | 2007130132 A | 5/2007 |

\* cited by examiner

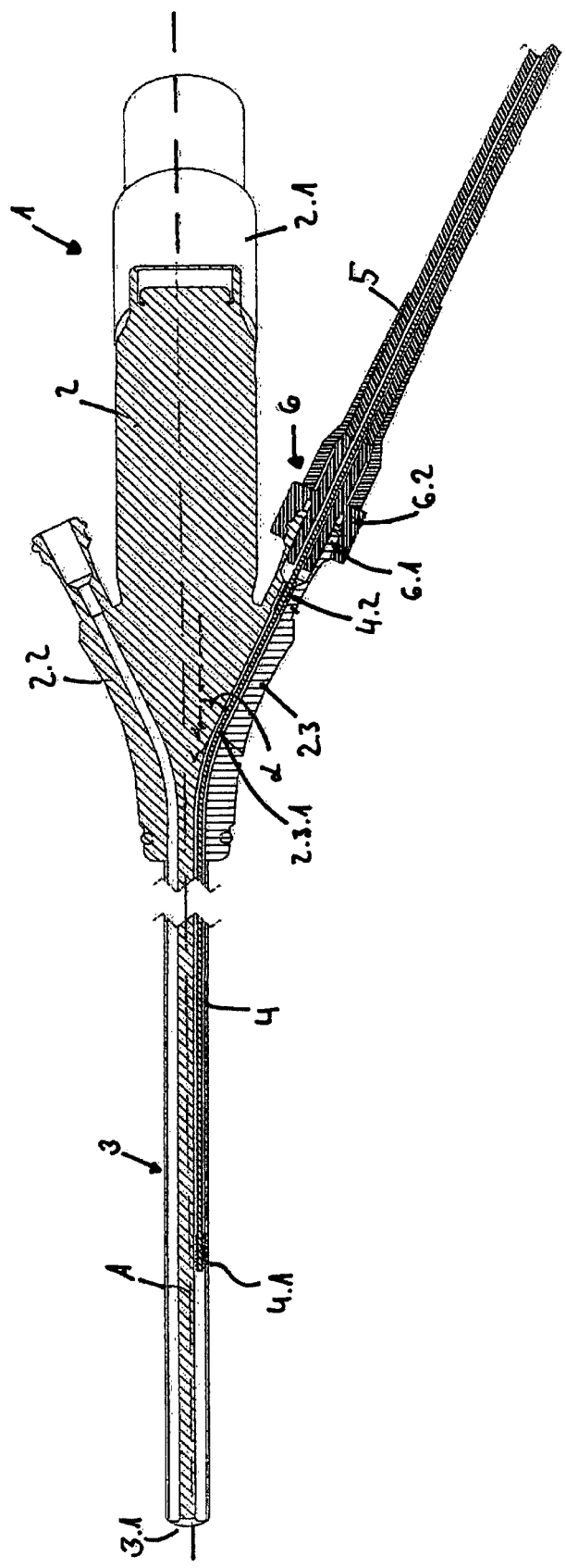

ENDOSCOPE DEVICE

CROSS REFERENCE TO RELATED APPLICATIONS

This application is a United States National Phase Application of International Application, PCT/EP2018/000405, filed Aug. 20, 2018, and claims the benefit of priority under 35 U.S.C. § 119 of German Applications 10 2017 008 148.4, filed Aug. 29, 2017 and 20 2017 004 822.1, filed Sep. 15, 2017, the entire contents of which are incorporated herein by reference.

TECHNICAL FIELD

The invention relates to an endoscope device having a proximal insertion head and having a shaft extending distally therefrom having a center axis, which extends with at least one oblong (elongated) lumen through the device.

TECHNICAL BACKGROUND

Minimally invasive operations are already carried out presently by means of navigation-assisted operating methods. Different navigation systems are used for this purpose. Active and passive systems are used. In active systems, a part introduced into the body of a patient, such as an instrument or surgical tool, is provided with a transmitter, via which the position of the instrument or tool, in particular the distal end located at the engagement location, may be externally determined. In passive systems, a field is generated, which is detected via a sensor, whereby the position and alignment of the instrument or surgical tool, in particular its distal end, can in turn be detected directly or indirectly. Direct detection of the distal end of a surgical part includes the arrangement of the sensor on the distal end of the part itself; indirect detection includes the fixed rigid attachment of the sensor in a defined point, in particular axial position, on the surgical part. Inferences about the position and possibly the orientation of the distal end can be seen on the basis of the measured sensor signal. In passive navigation, in particular electromagnetic navigation has proven itself, in which an electromagnetic field is generated externally around the operation region, for example, by a generator of an electromagnetic field in a cushion on which the patient lies. Coil-type sensors installed in the surgical part enable the locating of the instruments, whereupon a representation can be performed in CT or MRT images. This method does not include a radiation exposure and thus overall reduces the radiation exposure, also due to a reduced use of x-rays. The image quality is not impaired, nor can sensors be concealed, since they are not optical sensors. The freedom of movement of the operator is not restricted, as is the case with optical systems. The work of the operator is significantly facilitated.

SUMMARY

The invention is based on an object of providing a device, in which the location and orientation of an endoscope, in particular of the distal end, can be precisely determined using the above-described system while avoiding the mentioned disadvantages.

The mentioned object is achieved according to the invention by an endoscope device of the type mentioned at the outset, which is characterized by a sensor rod having at least two sensor coils arranged in the longitudinal direction at a finite spacing in relation to one another, which are oriented in relation to one another at a finite angle.

Because the two sensor coils are arranged at a finite angle in relation to one another in the endoscope device, because of the different arrangement, the orientation of the endoscope device in the magnetic field of the detection system and thus also in space can be precisely determined.

In one preferred embodiment, it is provided in this case that the first sensor coil is oriented in parallel in relation to the center axis and the second sensor coil is oriented at a finite angle in relation to the center axis, wherein in particular the first sensor coil is arranged in the shaft and the second sensor coil is arranged in an attachment of the insertion head.

In one refinement, it is provided that the rod bearing the two sensor coils extends through a lumen of the device, wherein in particular the rod is connected in an axially fixed manner to a holder which is attachable to the attachment of the insertion head. In this way, the location of the one sensor coil, in particular the first sensor coil, is accurately defined in the endoscope device and therefore on the basis of the determination of the location of the first sensor coil by the detection system in the magnetic field, the exact determination of the precise location of the distal end of the sensor device and thus of the working location is also possible, since the spacing of the (first) sensor coil from the distal end of the endoscope shaft is fixedly predetermined in this manner.

Due to the fixed connection of the rod bearing the sensor coil to a separable holder, furthermore, on the one hand, after positioning, the rod bearing the sensor coil is removed, and the lumen occupied thereby for the positioning can be released for other usage purposes. Furthermore, the sensor device formed by the rod having the sensor coils is thus separable from the actual endoscope and can be used in another way. This also enables simpler sterilization.

Further advantages and features of the invention result from the claims and from the following description, in which an exemplary embodiment of the invention is explained in detail with reference to the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE is a longitudinal sectional view of an endoscope device according to the invention.

DESCRIPTION OF PREFERRED EMBODIMENTS

Referring to the drawings, an endoscope device 1 according to the invention comprises in the illustrated exemplary embodiment a proximal insertion head 2 and a shaft 3 extending distally therefrom. In the illustrated exemplary embodiment, the insertion head 2 comprises three branches or attachments 2.1 to 2.3, namely one attachment 2.1 for introducing a light guide from the proximal end of the device 1 up to its distal end and also two attachments 2.2, 2.3, which each also comprise a lumen or a channel which extends from the distal end of the elongated shaft 3 with a center axis A up to an exit from the respective adapter 2.2, 2.3.

A rod 4, which bears two coils 4.1 and 4.2 with spacing in its longitudinal extension, extends through the lumen 2.3.1 of the attachment 2.3. The rod can be formed as a solid or flexible rod or also as a rod coiled in a helix. A connecting wire (not shown) extends from each of the coils 4.1, 4.2 in the proximal direction up to a respective proximal connecting or contact end of the respective wire, possibly in the formation of a plug for connection of the wires to an analysis unit (not shown).

The coil 4.1 is located at the distal end of the rod 4 and thus inside the shaft 3 extending in parallel to its center axis A and is therefore also oriented in parallel to the center axis A or axially-parallel. The coil 4.2 arranged with spacing in relation to the coil 4.1 on the rod 4 is located in the attachment 2.3 of the insertion head extending at a finite angle in relation to the center axis A. In that the lumen section of the lumen 2.3.1 also extends at a finite angle in relation to the center axis A, the orientation or extension of the coil 4.2 in the attachment 2.3 also encloses a finite angle in relation to the center axis A. The two coils 4.1, 4.2 are therefore not parallel to one another, but rather are oriented at a finite angle in relation to one another.

In the case of an externally applied inhomogeneous electromagnetic field, in which the coils 4.1, 4.2 are located, these coils therefore perceive the field differently and transmit different signals to the analysis unit. Due to this different orientation of the coils 4.1, 4.2, the orientation of the endoscope device in the electromagnetic field and thus in space can therefore be exactly determined.

The rod 4 is arranged axially fixed in a holder 5. The holder 5 and the attachment 2.3 are connectable to one another by a Luer adapter 6, wherein each of the parts bears a respective part 6.1, 6.2 corresponding to one another of the Luer adapter 6, so that the attachment 2.3 and the holder 5 can be fixedly connected to one another like a bayonet by the Luer adapter 6 in a way known per se. The location of the holder 5 in relation to the attachment 2.3 and also in relation to the head 2 and the shaft 3 of the endoscope device 1 is thus defined in the fastened state. Since the shaft 4, as stated, is arranged axially fixed in the holder 5, the longitudinal position of the coils 4.1, 4.2 and in particular of the distal coil 4.1 in the shaft 3 and thus the endoscope device 1 is therefore also defined and therefore the spacing, in particular the axial spacing of the coil 4.1 from the distal end 3.1 of the shaft 3, is also defined. By way of the sensor signal of the coil 4.1 in the applied electromagnetic field, its location and, because of the fixed spacing in relation to the distal end 3.1 of the shaft 3, the location of the distal end 3.1 of the shaft 3 in the electromagnetic field and thus in space can also thus be determined.

An operator therefore recognizes, on the basis of the analysis of the sensor signals and an image display on a display screen of the analysis unit, the position of the distal end 3.1 of the shaft 3 and thus also of the endoscope device 1 accurately and thus knows where exactly they are working with their instruments, which they possibly introduce into other lumens of the endoscope device and through them.

While specific embodiments of the invention have been shown and described in detail to illustrate the application of the principles of the invention, it will be understood that the invention may be embodied otherwise without departing from such principles.

The invention claimed is:
1. An endoscope device comprising:
   a proximal insertion head with an attachment of the insertion head;
   a shaft extending distally from the insertion head, the shaft having a center axis;
   at least one elongate lumen extending through the device; and
   a sensor rod having at least two sensor coils arranged at a finite spacing in relation to one another in a sensor rod longitudinal direction, the at least two sensor coils being oriented in relation to one another at a finite angle and wherein the at least two sensor coils comprise a first sensor coil oriented in parallel to the center axis and a second sensor coil located in the attachment of the insertion head and oriented at the finite angle in relation to the center axis.

2. An endoscope device according to claim 1, wherein the first sensor coil is arranged in the shaft.

3. An endoscope device according to claim 1, wherein the rod bearing the two sensor coils extends through the lumen.

4. An endoscope device according claim 1, further comprising a holder, wherein the holder is attachable to the attachment of the insertion head and the rod is connected axially fixed to the holder.

5. An endoscope device according to claim 4, wherein the attachment of the insertion head and the holder comprise corresponding Luer adapter parts facing toward one another forming a Luer adapter, and the attachment and the holder are fixedly connectable to one another by the Luer adapter.

6. An endoscope device according to claim 1, wherein the sensor rod further comprises a connecting wire that extends from each sensor coil through the rod up to a sensor rod proximal end for connection to an analysis unit.

7. An endoscope device comprising:
   a proximal insertion head with an attachment of the insertion head;
   a shaft extending distally from the insertion head, the shaft having a center axis, wherein the attachment of the insertion head extends at a finite angle with respect to the center axis;
   at least one elongate lumen extending through the device, the lumen having a lumen section that extends in the attachment of the insertion head and at a finite angle in relation to the center axis;
   a sensor rod;
   a first sensor coil supported by the sensor rod and located at a distal end of the sensor rod, inside the shaft, and extending in parallel to the center axis and oriented in parallel to the center axis; and
   a second sensor coil supported by the sensor rod and arranged with a spacing in relation to the first sensor coil at the sensor rod and located in the attachment of the insertion head, the attachment of the insertion head extending at a finite angle in relation to the center axis, wherein an orientation or extension of the second sensor coil in the attachment of the sensor head also encloses a finite angle in relation to the center axis and the first sensor coil and the second sensor coil are not parallel to one another and the second sensor coil is oriented at a finite angle in relation to the first sensor coil, wherein the rod bearing the two sensor coils extends through the lumen with the second sensor coil arranged in the lumen section extending at the finite angle in relation to the center axis.

8. An endoscope device according claim 7, further comprising a holder attachable to the attachment of the insertion head, wherein the rod is axially fixed to the holder whereby upon attaching the holder to the attachment, the first sensor coil is located at a predefined position inside the shaft and the second sensor coil is located at a predefined position inside the lumen section extending at the finite angle in relation to the center axis.

9. An endoscope device according to claim 8, wherein the attachment of the insertion head and the holder comprise corresponding Luer adapter parts facing toward one another forming a Luer adapter, and the attachment and the holder are fixedly connectable to one another by the Luer adapter to set the defined positions in a fixed state.

10. An endoscope device according to claim 7, wherein the sensor rod further comprises a connecting wire that extends from each sensor coil through the rod up to a sensor rod proximal end for connection to an analysis unit.

11. An endoscope device comprising:
    a proximal insertion head with an attachment of the insertion head;
    a shaft extending distally from the insertion head, the shaft having a center axis;
    at least one elongate lumen extending through the device, the lumen having a lumen section that extends in the attachment of the insertion head and at a finite angle in relation to the center axis
    a sensor rod;
    a first sensor coil supported by and located at the distal end of the sensor rod, inside the shaft, and extending in parallel to the center axis and oriented in parallel to the center axis;
    a second sensor coil supported by and arranged with a spacing in relation to the first sensor coil at the sensor rod and located in the attachment of the insertion head, the attachment of the insertion head extending at a finite angle in relation to the center axis, wherein an orientation or extension of the second sensor coil in the attachment of the sensor head also encloses a finite angle in relation to the center axis and the first sensor coil and the second sensor coil are not parallel to one another and the second sensor coil is oriented at a finite angle in relation to the first sensor coil, wherein the rod bearing the two sensor coils extends through the lumen with the second sensor coil arranged in the lumen section extending at the finite angle in relation to the center axis; and
    a holder attachable to the attachment of the insertion head, wherein the rod is axially fixed to the holder whereby upon attaching the holder to the attachment, the first sensor coil is located at a predefined position inside the shaft and the second sensor coil is located at a predefined position inside the lumen section extending at the finite angle in relation to the center axis.

12. An endoscope device according to claim 11, wherein the attachment of the insertion head and the holder comprise corresponding Luer adapter parts facing toward one another forming a Luer adapter, and the attachment and the holder are fixedly connectable to one another by the Luer adapter to set the defined positions in a fixed state.

13. An endoscope device according to claim 12, wherein the sensor rod further comprises a connecting wire that extends from each sensor coil through the rod up to a sensor rod proximal end for connection to an analysis unit.

* * * * *